(12) United States Patent
Bitzer

(10) Patent No.: US 9,913,683 B2
(45) Date of Patent: Mar. 13, 2018

(54) CATHETER ARRANGEMENT AND METHOD FOR DETERMINING A FORCE APPLIED TO A CATHETER END

(71) Applicant: VascoMed GmbH, Binzen (DE)

(72) Inventor: Andreas Bitzer, Zurich (CH)

(73) Assignee: VascoMed GmbH, Binzen (DE)

( * ) Notice: Subject to any disclaimer, the term of this patent is extended or adjusted under 35 U.S.C. 154(b) by 400 days.

(21) Appl. No.: 14/335,420

(22) Filed: Jul. 18, 2014

(65) Prior Publication Data
US 2015/0051600 A1    Feb. 19, 2015

Related U.S. Application Data

(60) Provisional application No. 61/866,052, filed on Aug. 15, 2013.

(51) Int. Cl.
*A61B 18/14* (2006.01)
*G01L 7/04* (2006.01)
(Continued)

(52) U.S. Cl.
CPC ............ *A61B 18/1492* (2013.01); *G01L 1/04* (2013.01); *G01L 7/041* (2013.01);
(Continued)

(58) Field of Classification Search
CPC ...... A61B 18/1492; A61B 2018/00029; A61B 2218/002; A61B 2018/00577;
(Continued)

(56) References Cited

U.S. PATENT DOCUMENTS

| 5,399,854 | A | 3/1995 | Dunphy et al. | |
|---|---|---|---|---|
| 2002/0123749 | A1* | 9/2002 | Jain | A61B 18/1492 606/41 |
| 2008/0161794 | A1* | 7/2008 | Wang | A61B 18/1492 606/41 |
| 2008/0285909 | A1 | 11/2008 | Younge et al. | |
| 2011/0270246 | A1* | 11/2011 | Clark | A61B 18/1492 606/41 |
| 2012/0220879 | A1 | 8/2012 | Fandrey et al. | |
| 2013/0150805 | A1* | 6/2013 | Boomsma | A61M 3/0279 604/246 |

(Continued)

FOREIGN PATENT DOCUMENTS

| EP | 2 604 209 | 6/2013 |
|---|---|---|
| WO | 2008003307 | 1/2008 |

(Continued)

OTHER PUBLICATIONS

European Search Report and Notes to the European Search Report on European Patent Application EP 14 17 7423, dated Feb. 23, 2015 (5 pages).

*Primary Examiner* — Jaymi Della
(74) *Attorney, Agent, or Firm* — Buchanan Ingersoll & Rooney PC

(57) ABSTRACT

A catheter arrangement including a catheter having a proximal end and a distal end and at least one continuous fluid channel, at the proximal end of which a fluid connection and at the distal end of which a nozzle is arranged, which has a cross section that can be varied by a force applied to the distal catheter end; a liquid feed unit, connected to the proximal fluid connection of the catheter feeds liquid into the at least one fluid channel at a predetermined operating pressure. A flow sensor measures, during operation of the catheter arrangement, a pressure drop at the fluid channel. A pressure evaluation unit, connected on the input side in a signal-based manner to the flow sensor, determines a force applied to the distal end of the catheter from the measured pressure drop at the fluid channel and from predetermined deformation characteristics of the associated nozzle.

15 Claims, 2 Drawing Sheets

(51) Int. Cl.
*G01L 1/04* (2006.01)
*A61B 18/00* (2006.01)
*A61B 90/00* (2016.01)

(52) U.S. Cl.
CPC ............... *A61B 2018/00029* (2013.01); *A61B 2018/00577* (2013.01); *A61B 2018/00773* (2013.01); *A61B 2018/00863* (2013.01); *A61B 2018/00875* (2013.01); *A61B 2090/065* (2016.02); *A61B 2218/002* (2013.01)

(58) Field of Classification Search
CPC ........... A61B 2018/00773; A61B 2018/00863; A61B 2018/00875; A61B 5/6843; A61B 2090/065; G01L 1/04; G01L 7/041
See application file for complete search history.

(56) References Cited

U.S. PATENT DOCUMENTS

| | | | |
|---|---|---|---|
| 2013/0172784 A1* | 7/2013 | Kirschenman | ....... A61B 5/6843 600/587 |
| 2014/0081264 A1 | 3/2014 | Fandrey et al. | |
| 2014/0209797 A1* | 7/2014 | Klimovitch | ............ G01B 11/16 250/227.14 |

FOREIGN PATENT DOCUMENTS

| | | |
|---|---|---|
| WO | 2009007857 | 1/2009 |
| WO | 2009138957 | 11/2009 |

\* cited by examiner

CATHETER ARRANGEMENT AND METHOD FOR DETERMINING A FORCE APPLIED TO A CATHETER END

CROSS-REFERENCE TO RELATED APPLICATIONS

This patent application claims the benefit of U.S. Provisional Patent Application No. 61/866,052, filed on Aug. 15, 2013, which is hereby incorporated by reference in its entirety.

TECHNICAL FIELD

The present invention relates to a catheter arrangement, which comprises a catheter having a proximal end and a distal end and at least one continuous fluid channel, at the proximal end of which a fluid connection is arranged, and which further comprises a liquid feed unit connected to the fluid connection. The present invention also relates to a method for determining a force applied to the distal end of a corresponding catheter.

BACKGROUND

In specific fields of use of catheters or similar devices, for example, electrode lines, a contact pressure against adjacent tissue is significant for the function of the catheter or similar device, such that a measurement of this contact force is of interest. This is applicable, to a particular extent, for what are known as ablation catheters, with which areas of tissue or tissue parts are removed.

An ablation catheter (e.g., "TactiCath" manufactured by Endosense) is known that enables measurement, during an ablation procedure, of the magnitude and direction of a force applied to the distal catheter end—during use that is to say the mentioned contact force. This catheter utilizes the principle of what is known as the FBG (Fiber Bragg Grating) sensor, wherein three fibers, each having an FBG sensor at the fiber end, form the group of sensors required for a 3D force measurement, it being possible to incorporate said sensors for joint measurement signal processing on a signal processing machine. The sensors are attached externally on a deformable cylinder at an angular distance of 120°.

In U.S. Publication No. 2008/0285909, the operating principle of FBG sensors for determining twists or curvatures of the catheter body is described in detail, and the operating mode of the aforementioned force sensor having a plurality of FBG fibers on a deformable cylinder is also explained in this document.

As described in International Publication No. WO 2009/138957, a temperature compensation is provided by means of three electrical thermocouples, because, in the case of the FBG measurement method, even small changes in temperature or deviations between the individual sensors can cause severe measurement uncertainties and, in the case of an electrothermal ablation procedure, rather considerable temperature fluctuations at the tip of the ablation catheter can occur.

The optical measurement principle of the FBG sensor is known in general and, in particular, also in its application for force measurements and temperature measurements; for example see "www.wikipedia.org/wiki/Fiber_Bragg_grating" or A. Othonos, K. Kalli: *"Fiber Bragg Gratings: Fundamentals and Applications in Telecommunications and Sensing"* Artec House 1999, and (specifically based on voltage measurements and temperature measurements) U.S. Pat. No. 5,399,854. A detailed explanation of the FBG sensor measurement principle is therefore not necessary here.

Irrespective of this measurement principle, other solutions for a contact force measurement on a guide wire or catheter are also known, for example, with use of an optical sensor, as described in International Publication No. WO 2009/007857, or with use of a semiconductor sensor at the tip of a guide wire, as described in International Publication No. WO 2008/003307.

More recent improvements to the aforementioned solutions are the subject of U.S. Publication No. 2012/0220879 and U.S. Application No. 61/703,272, also in the name of the Applicant herein.

The present invention is directed toward overcoming one or more problems associated with current catheters.

SUMMARY

An object of the present invention is to specify a catheter arrangement of the type mentioned in the introduction that has a simplified design and is therefore cost effective. Furthermore, a sufficiently reliable measurement method of the above-mentioned type that can be implemented with a simple cost-effective design is also to be provided.

At lease this object is achieved with regard to its device aspect by a catheter arrangement having the features of independent claim 1 and, in terms of its method aspect, by a method having the features of independent claim 13. Expedient developments of the inventive concept are disclosed in the respective dependent claims. A catheter and also a liquid feed unit and also a pressure evaluation unit for forming a catheter arrangement according to claim 1 and also variants of these components of the catheter arrangement are also claimed.

The present invention includes the consideration of specifying a catheter arrangement in which the contact force between a catheter tip and the tissue bearing there against can be determined and which has a very low level of complexity so as to be producible in a cost-efficient and automated manner. Here, an optical or electronic sensor that is attached in the catheter is to be completely omitted.

The measurement sensor necessary for the force measurement, in accordance with a further aspect of the invention, is to be housed primarily in an external unit, which external unit is not brought into contact directly with the patient and can therefore be reused. In addition, the solution is to enable automated production to the greatest possible extent due to the use of simple component parts.

This provides the design of the arrangement according to the present invention which, in particular, comprises a catheter fabricated as a disposable or throw-away article and, as further components, a liquid feed unit and evaluation unit that can be used over relatively long periods of time. Significant advantages compared to known systems can be produced with the present invention, in particular as follows:

There is a high cost savings since costly optical and electronic measurement technology in the region of the disposable components (e.g., catheter) of a catheter system of this type can be omitted.

The system is more environmentally sound.

The system can be produced in an automated manner, since the catheter has a channel system, which can be produced in an extremely cost-effective manner by means of an extrusion method. Here, the complexity is rooted exclusively in the singular embodiment of the tool. In addition, the discharge nozzles can be produced in an extremely accurate and cost-effective manner by means of laser machining, for example.

The system dispenses completely with costly optical measurement technology, such as the FBG sensors, where the sensors are read out by means of spectroscopy.

The present invention makes it possible to provide a catheter arrangement that, in terms of cost, is not much more expensive than previous catheters without force measurement functionality, whereby an enormous market advantage could be provided for the future.

The present invention is based on the concept of a force measurement by means of hydrodynamic flow measurement of a liquid flowing through a nozzle, wherein the nozzle is designed such that it has an opening cross section which is dependent on an external force. In a particularly suitable embodiment, the liquid can be formed directly by cooling liquid.

To explain the usefulness of this concept, the Hagen-Poiseuille law will be used as a basis. In accordance with the Hagen-Poiseuille law:

$$j = \frac{\pi r^4 \Delta P}{8 \eta l}$$

$j$ [m^3/s]
$r$ [m]
$l$ [m]
$P$ [pascal]

Conversion of the flow:
1 m^3/s=6 10^13 nl/min
Assumptions:
  catheter length L=2 m
  diameter of the fluid channel R=300 μm=300 10^-6 m
  viscosity of water η=1
  pressure difference dP=2 bar=2 10^5 pascal
  nozzle bore r=10 μm=10*10^-6 m
  length of the nozzle bore l=100 μm=100*10^-6 m
  measurement limits for flow measurements of a commercially available flow sensor: 0.5 nl/min In order to ensure the function of the force measurement sensor described herein, it must firstly be ensured that the change to the flow is induced primarily by a variation of the nozzle diameter and not by other influences, for example, such as a change to the tube cross section. The greatest resistance must therefore be provided by the nozzle. This means that the greatest pressure drop must occur via the nozzle region and not via the feed of the liquid to the nozzle.

In order to illustrate this, it is recommended to divide the liquid path into two portions: the tube system (length L=2 m, D=0.5 mm) which conducts the liquid to the nozzle, and the nozzle portion itself (l=200 μm, d=20 μm).

In accordance with the principle of hydrodynamic continuity, the flow j must be the same throughout the system. In accordance with the Hagen-Poiseuille principle, the pressure distribution over the two portions can be calculated as follows:

$$j = \frac{\pi r_{nozzle}^4 \Delta P_{nozzle}}{8 \eta l_{nozzle}}$$

-continued $$j = \frac{\pi r_{tube}^4 \Delta P_{tube}}{8 \eta l_{tube}}$$

Balancing of the two equations gives:

$$\frac{\Delta P_{nozzle}}{\Delta P_{tube}} = \frac{r_{tube}^4 l_{nozzle}}{r_{nozzle}^4 l_{tube}} = \frac{(300 \text{ μm})^4 200 \text{ μm}}{(10 \text{ μm})^4 2 \text{ m}} = 81$$

This means that the pressure drop with the assumed values, which have been selected such that they would satisfy a catheter construction, at the nozzle is 81 times greater than that produced via the tube system.

Furthermore, the dynamic range of the flow sensor has to be utilized reasonably. For this, we assume that the pressure drop via the nozzle is to be 2 bar. For the flow produced with a pressure difference of 2 bar at the nozzle in accordance with the above-stated values, the following is true:

$$j = \frac{\pi r^4 \Delta P_{nozzle}}{8 \eta l_{nozzle}} = \frac{\pi (10 \text{ μm})^4 2 \cdot 10^5 \text{ pascal}}{8 \cdot 1 \cdot 200 \text{ μm}} = 3.92 \cdot \frac{10^{-12} \text{m}^3}{\text{s}} = \frac{236 \text{ nl}}{\text{min}}$$

Compared with the measurement accuracy of the sensor of 0.5 nl/min, this comparison shows that the flow could therefore be determined very effectively.

To finish, it will also be demonstrated how the flow would change as a result of a change of 10% of the nozzle cross section.

If the cross section thus reduces to 0.9 of the original value, a decrease of 0.9^4=0.65 is thus given. This means that instead of the original 236 nl/min, only 155 nl/min would still flow out—a change that could be measured very effectively with the sensor, which has a resolution of 0.5 nl/min.

Generally, it would also be conceivable however to work with higher flow rates up to, for example, 1 ml/min. At the low flow rates, the change in length of the overall tube specifically could have a negative effect. If this tube is bent by the pull wire, the volume would thus also be compressed. Rough estimation has revealed that the flow rate thus produced would account for approximately 1 μl/min. With measured flows of 236 nl/min, this influence would already be considerable and would disrupt the measurement significantly.

In an embodiment of the present invention, the catheter has at least three fluid channels, in particular, arranged at equal angular distances in relation to one another and each having a proximal fluid connection and a distal nozzle with variable cross section; and the liquid feed unit has three flow sensors, each of which is associated with one of the three fluid channels provided with distal nozzles; and the pressure evaluation unit is formed with three channels for the evaluation of the signals of the three flow sensors for calculation of a force vector of the force applied to the distal catheter end. In a variant of this embodiment, the three fluid channels provided with associated flow sensors have the same cross section and the nozzles provided at the distal end thereof have the same nozzle shape.

In a further variant, the, or each, nozzle is arranged adjacently from the outermost distal end of the catheter, and a catheter portion formed from resiliently deformable material is arranged in the vicinity of the nozzle in such a way that an application of force onto the outer most distal end leads to a proportional reduction of the nozzle cross section. In a variant, the, or each, nozzle is slit-shaped and extends substantially perpendicular to the longitudinal axis of the catheter.

In an embodiment of the arrangement that is important from a practical point of view, the catheter is formed as an ablation catheter comprising at least one ablation electrode, and the, or each, fluid channel is formed as a flushing channel and the nozzle provided at its distal end is arranged adjacently to the ablation electrode.

A deformation characteristic memory for storing a set of values of deformation characteristic of the, or each, nozzle is expediently provided in the pressure evaluation unit together with a processing component, in which an evaluation algorithm for determining the applied force is implemented from the stored set of deformation characteristics.

In a variant of the proposed method in which, with use of a catheter comprising at least three fluid channels arranged, in particular, at equal angular distances in relation to one another and each having a proximal fluid connection and a distal nozzle with variable cross section, a force vector of the effective force is determined, a liquid feed unit having three flow sensors each associated with a fluid channel is connected and, in a three-channel pressure evaluation unit connected on the input side in a signal-based manner to the flow sensors, the signals of the three flow sensors are used to calculate the force vector.

Further features, aspects, objects, advantages, and possible applications of the present invention will become apparent from a study of the exemplary embodiments and examples described below, in combination with the Figure, and the appended claims.

DESCRIPTION OF THE DRAWINGS

Advantages and expedient features of the present invention will also emerge from the following description of exemplary embodiments with reference to the figures, in which.

DETAILED DESCRIPTION

Figure 1:
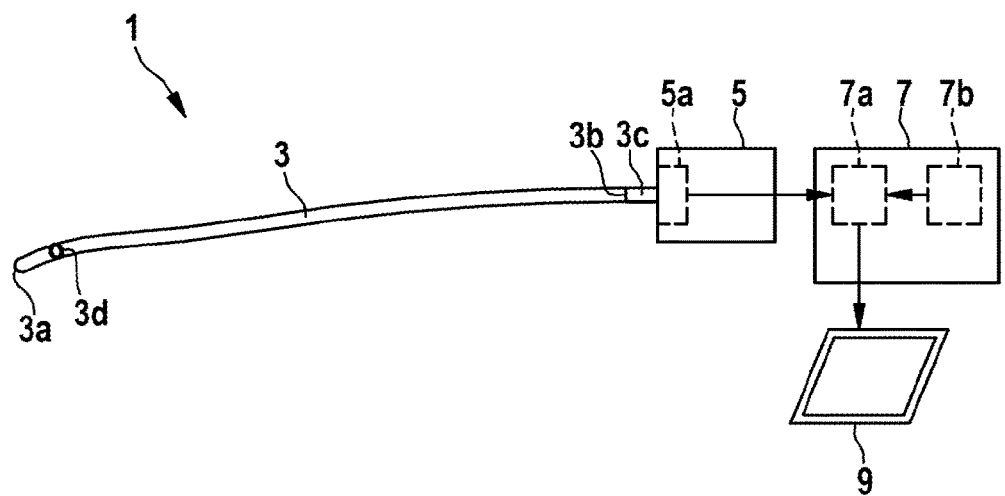
FIG. 1 shows a rough illustration of a catheter arrangement according to an embodiment of the present invention.

FIG. 1 shows a schematic view of a catheter arrangement 1, which comprises a tubular catheter 3 having a distal end 3a and a proximal end 3b, at the proximal end 3b of which a fluid connection 3c and in the vicinity of the distal end 3a of which a nozzle opening 3d are arranged. A liquid feed unit 5 having a design known in principle, as is conventional with corresponding units of flushed ablation catheters, is connected to the fluid connection 3c of the catheter 3. A particular feature of the liquid feed unit 5 lies in the presence of a flow sensor 5a associated with the fluid connection 3c of the catheter 3, it being possible to quantitatively measure a pressure drop in a fluid channel (not illustrated here) in the catheter 3 by means of said flow sensor 5a.

The flow sensor 5a is connected in a signal-based manner to a pressure evaluation unit 7, more specifically to a processing component 7a thereof. The processing component 7a, in which an evaluation algorithm for processing pressure drop values measured by means of the flow sensor 5a is implemented, is associated with a memory unit 7b, in which evaluation-relevant characteristics (parameters) of the catheter 3 are stored. The output of the processing component 7a is connected to a display unit 9, on which values (magnitude values or vector components), calculated from the pressure drop values, of an external force applied to the distal catheter end 3a can be displayed.

Figure 2:
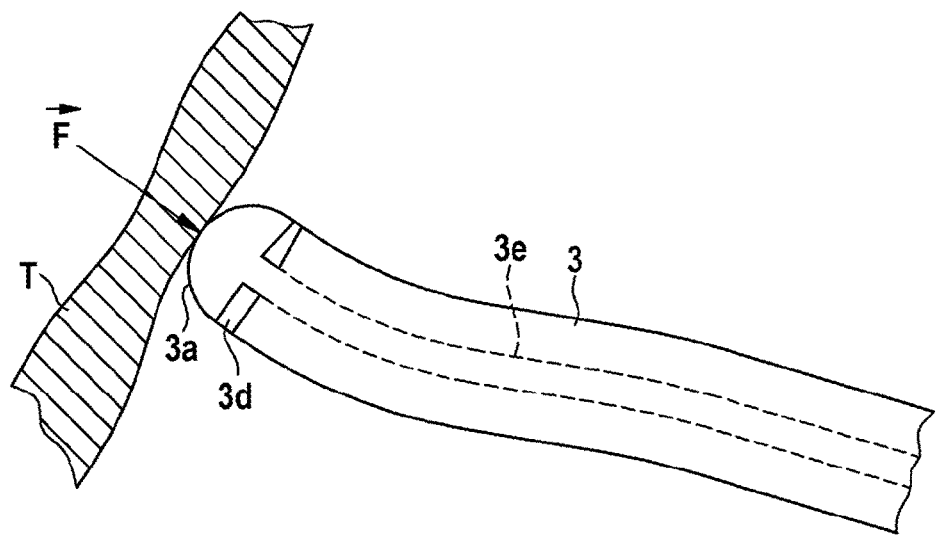
FIG. 2 shows a rough illustration of the distal catheter end in contact with an organ wall or vessel wall exerting a force.

FIG. 2 shows a situation of use of the catheter 3 with enlarged illustration of the nozzle 3d arranged at a short distance from, or at, the distal end 3a. Here, the above-mentioned fluid channel 3e (not illustrated in FIG. 1, however) that runs from the proximal fluid connection 3c to the nozzle 3d is also shown. With contact between the catheter end 3a and an organ wall or vessel wall T, a force F is exerted by said wall onto the catheter end 3a. With an appropriate dimensionally resilient embodiment of the distal catheter portion, this application of force leads to a deformation, more specifically a cross-sectional reduction over portions, of the nozzle 3d. As explained in greater detail further above, this in turn leads to a pressure change in the fluid system of the catheter arrangement, which can be detected by means of the flow sensor 5a.

Figure 3:
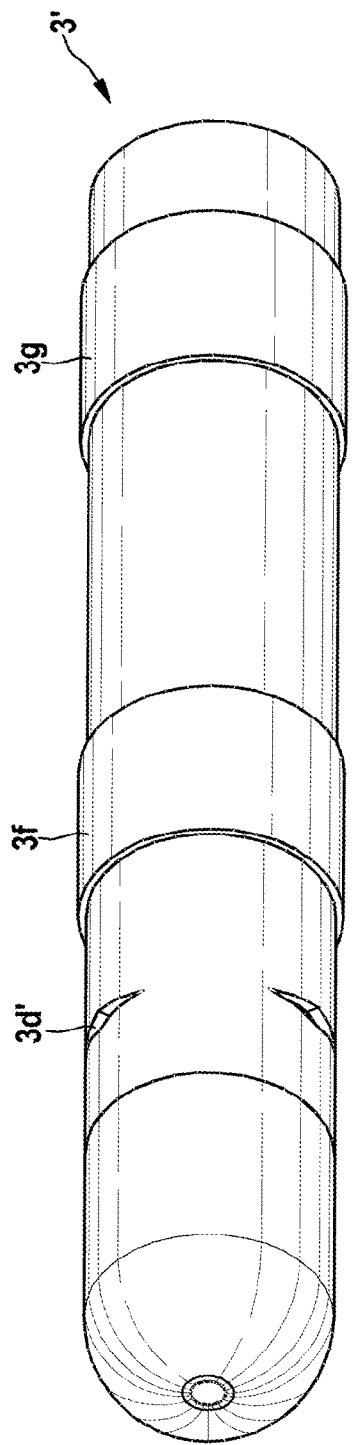
FIGS. 3-4 show an external view and a partly cut-away view of a distal catheter end of another embodiment in accordance with the present invention.
Figure 4:
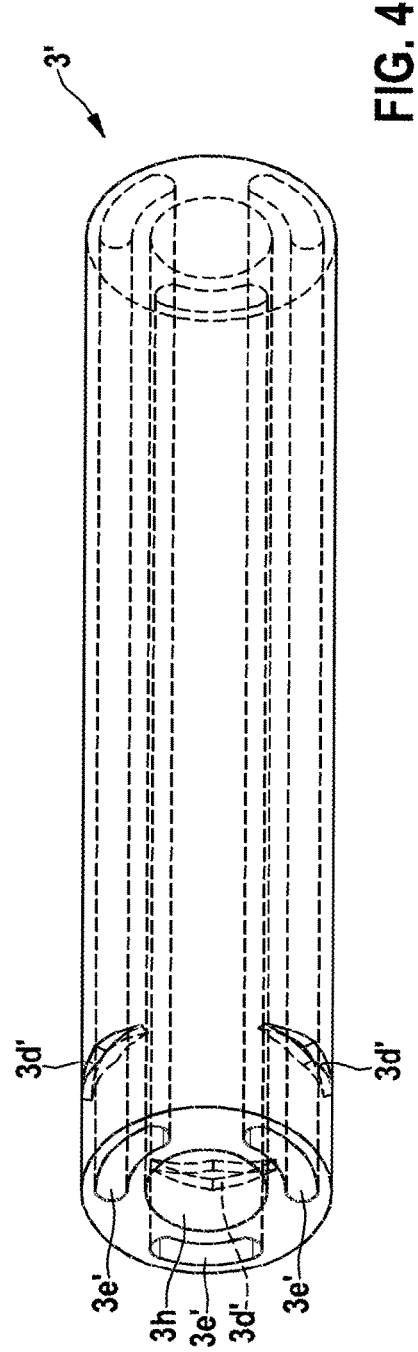

FIGS. 3 and 4 shows the distal end of a modified catheter 3', which is equipped with two interspaced ablation electrodes (ring electrodes) 3f, 3g arranged in the distal end region. Besides a central lumen 3h, in which parts can normally be housed that are not of significance for the implementation of the present invention, three fluid channels 3e' are arranged at equal angular distances in the catheter body and are each associated with a discharge nozzle 3d' and also, at the proximal catheter end, a fluid connection. Distally from the slit-shaped nozzles 3d', the fluid channels 3e' are each closed, such that liquid introduced from the proximal end into the fluid channels has to escape completely via the nozzles 3d'.

With a force that is applied directly from the front onto the system (i.e., the catheter 3, 3'), all nozzles 3d' would be compressed. If, by contrast, a force is applied from the lateral direction onto the system, this would thus cause an asymmetrical compression or stretching. On the basis of an imaging matrix, the force vector applied to the system can thus be calculated from the three sensor values. The fluid channels 3e' have a matching cross section, and the nozzles 3d' also have the same shape, such that the same pressure conditions prevail in all fluid channels in a state of the catheter free from applications of external force. With the application of an external force, the nozzles 3d' deform in accordance with the vector components of this force, such that the pressure drop values measured in the individual fluid channels 3e' (in each case via an associated flow sensor 5a) make it possible to ascertain the vector components and therefore ultimately to determine the applied force in an approximately vector-based manner.

The embodiment of the present invention is not limited to the above-described examples and emphasized aspects, but can also be implemented in a large number of modifications that lie within the scope of the capabilities of a person skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A catheter arrangement, which comprises:
    a catheter having a proximal end and a distal end and at least one continuous fluid channel extending from the proximal end to the distal end, the proximal end of the catheter having a fluid connection and the distal end of the catheter having at least one nozzle, wherein the at least one nozzle has a cross-section that can be varied by a force applied to the catheter distal end,
    a liquid feed unit, connected to the fluid connection of the catheter for feeding liquid into the at least one continuous fluid channel of the catheter at a predetermined operating pressure, wherein, in the liquid feed unit, at least one flow sensor for measuring, during operation of the catheter arrangement, a pressure drop at the at least one continuous fluid channel through which the liquid flows is provided, and
    a pressure evaluation unit, connected on an input side in a signal based manner to the at least one flow sensor, for determining the force applied to the catheter distal end from the pressure drop at the at least one continuous fluid channel and from predetermined deformation characteristics of the at least one nozzle via detection and evaluation of signals from the at least one flow sensor,
    wherein the at least one continuous fluid channel comprises at least three continuous fluid channels extending from the proximal end to the distal end of the catheter,
    wherein the at least one nozzle comprises at least three nozzles in fluid communication, one each, with the at least three continuous fluid channels,
    wherein distally of the at least three nozzles the at least three continuous fluid channels are closed, such that liquid introduced from the proximal end into the at least three continuous fluid channels must escape completely via the respective at least three nozzles,
    wherein the at least one flow sensor comprises at least three flow sensors
    wherein the at least three flow sensors are assigned, one each, to the at least three continuous fluid channels for measuring, during operation of the catheter arrangement, a pressure drop at a respective continuous fluid channel through which the liquid flows, and
    wherein the pressure evaluation unit is formed with at least three channels for evaluating the signals from the at least one flow sensor for calculating a force vector of a force applied to the distal end of the catheter.

2. The catheter arrangement as claimed in claim 1, wherein the at least three continuous fluid channels are arranged at equal angular distances in relation to one another.

3. The catheter arrangement as claimed in claim 2, wherein each of the at least three continuous fluid channels has a same cross section, and wherein each of the at least three nozzles has a same nozzle shape.

4. The catheter arrangement as claimed in claim 1, wherein the at least three nozzles are arranged adjacently to an outermost distal end of the catheter, and wherein a catheter portion formed from resiliently deformable material is arranged in a vicinity of the at least three nozzles in such a way that an application of the force on the outermost distal end leads to a proportional reduction of the cross section of at least one of the at least three nozzles.

5. The catheter arrangement as claimed in claim 4, wherein the at least three nozzles are slit shaped and extend perpendicular to a longitudinal axis of the catheter.

6. The catheter arrangement as claimed in claim 1, wherein the catheter is formed as an ablation catheter with at least one ablation electrode, and wherein the at least three continuous fluid channels are formed as flushing channels, and wherein the at least three nozzles are arranged adjacently to the at least one ablation electrode.

7. The catheter arrangement as claimed in claim 1, wherein a deformation characteristic memory for storing a set of values of deformation characteristics of the at least three nozzles is provided in the pressure evaluation unit together with a processing component, in which an evaluation algorithm for determining the force is implemented from the stored set of values of deformation characteristics.

8. The catheter arrangement as claimed in claim 1, wherein the at least three nozzles are arranged adjacently to an outermost distal end of the catheter.

9. The catheter arrangement as claimed in claim 8, wherein the catheter is formed as an ablation catheter having at least one ablation electrode, wherein the at least three continuous fluid channels are formed as flushing channels and the at least three nozzles are arranged adjacently to the at least one ablation electrode.

10. A liquid feed unit for fowling a catheter arrangement, the catheter arrangement comprising:
    a catheter having a proximal end and a distal end and at least one continuous fluid channel extending from the proximal end to the distal end, the proximal end of the catheter having a fluid connection and the distal end of the catheter having at least one nozzle, wherein the at least one nozzle has a cross-section that can be varied by a force applied to the catheter distal end,
    a liquid feed unit, connected to the fluid connection of the catheter for feeding liquid into the at least one continuous fluid channel of the catheter at a predetermined operating pressure, wherein, in the liquid feed unit, at least one flow sensor for measuring, during operation of the catheter arrangement, a pressure drop at the at least one continuous fluid channel through which the liquid flows is provided, and
    a pressure evaluation unit, connected on an input side in a signal based manner to the at least one flow sensor, for determining the force applied to the catheter distal end from the pressure drop at the at least one continuous fluid channel and from predetermined deformation characteristics of the at least one nozzle via detection and evaluation of signals from the at least one flow sensor,
    wherein the at least one continuous fluid channel comprises at least three continuous fluid channels extending from the proximal end to the distal end of the catheter,
    wherein the at least one nozzle comprises at least three nozzles in fluid communication, one each, with the at least three continuous fluid channels,
    wherein distally of the at least three nozzles the at least three continuous fluid channels are closed, such that liquid introduced from the proximal end into the at least three continuous fluid channels must escape completely via the respective at least three nozzles,
    wherein the at least one flow sensor comprises at least three flow sensors,
    wherein the at least three flow sensors are assigned, one each, to the at feast three continuous fluid channels for measuring, during operation of the catheter arrangement, a pressure drop at a respective continuous fluid channel through which the liquid flows, and wherein the pressure evaluation unit is formed with at least three channels for evaluating the signals from the at least one flow sensor for calculating a force vector of a force applied to the distal end of the catheter, wherein the liquid feed unit has the at least one flow sensor for each of the at least three continuous fluid channels.

11. A pressure evaluation unit for forming a catheter, the catheter arrangement comprising:

a catheter having a proximal end and a distal end and at least one continuous fluid channel extending from the proximal end to the distal end, the proximal end of the catheter having a fluid connection and the distal end of the catheter having at least one nozzle, wherein the at least one nozzle has a cross-section that can be varied by a force applied to the catheter distal end, a liquid feed unit, connected to the fluid connection of the catheter for feeding liquid into the at least one continuous fluid channel of the catheter at a predetermined lined operating pressure, wherein, in the liquid feed unit, at least one flow sensor for measuring, during operation of the catheter arrangement, a pressure drop at the at least one continuous fluid channel through which the liquid flows is provided, and a pressure evaluation unit, connected on an input side in a signal based manner to the at least one flow sensor, for determining the force applied to the catheter distal end from the pressure drop at the at least one continuous fluid channel and from predetermined deformation characteristics of the at least one nozzle via detection and evaluation of signals from the at least one flow sensor, wherein the at least one continuous fluid channel comprises at least three continuous fluid channels extending from the proximal end to the distal end of the catheter, wherein the at least one nozzle comprises at least three nozzles in fluid communication, one each, with the at least three continuous fluid channels, wherein distally of the at least three nozzles the at least three continuous fluid channels are closed, such that liquid introduced from the proximal end into the at least three continuous fluid channels must escape completely via the respective at least three nozzles, wherein the at least one flow sensor comprises at least three flow sensors, wherein the at least three flow sensors are assigned, one each, to the at least three continuous fluid channels for measuring, during operation of the catheter arrangement, a pressure drop at a respective continuous fluid channel through which the liquid flows, and wherein the pressure evaluation unit is formed with at least three channels for evaluating the signals from the at least one flow sensor for calculating a force vector of a force applied to the distal end of the catheter, wherein the pressure evaluation unit comprises a display unit.

12. The pressure evaluation unit as claimed in claim 11, wherein a deformation characteristic memory for storing a set of values of deformation characteristics of the at least three nozzles is provided together with a processing component, in which an evaluation algorithm for determining the force is configured to be implemented from the stored set of values of deformation characteristics.

13. The liquid feed unit as claimed in claim 10, wherein the at least three continuous fluid channels are arranged at equal angular distances in relation to one another.

14. The pressure evaluation unit as claimed in claim 11, wherein the at least three continuous fluid channels are arranged at equal angular distances in relation to one another.

15. A method for determining a force applied to the distal end of a catheter having a proximal end and a distal end and at least one continuous fluid channel extending from the proximal end to the distal end, the proximal end of the catheter having a fluid connection and the distal end of the catheter having at least one nozzle, wherein the at least one nozzle has a cross section that can be varied by a force applied to the catheter distal end, wherein, at the proximal fluid connection of the catheter, a liquid feed unit for feeding liquid into the at least one continuous fluid channel of the catheter at a predetermined operating pressure is connected, the method comprising:

measuring a pressure drop at the at least one continuous fluid channel through which the liquid flows during operation of the catheter via at least one flow sensor in the liquid feed unit; and determining the force applied to the catheter distal end from the measured pressure drop at the at least one continuous fluid channel and from predetermined deformation characteristics of the at least one nozzle by a pressure evaluation unit connected on an input side in a signal based manner to the flow sensor via detection and evaluation of signals from the at least one flow sensor, wherein the at least one continuous fluid channel comprises at least three continuous fluid channels extending from the proximal end to the distal end of the catheter, wherein the at least one nozzle comprises at least three nozzles in fluid communication, one each, with the at least three continuous fluid channels, wherein distally of the at least three nozzles the at least three continuous fluid channels are closed, such that liquid introduced from the proximal end into the at least three continuous fluid channels must escape completely via the respective at least three nozzles, wherein the at least one flow sensor comprises at least three flow sensors, wherein the at least three flow sensors are assigned, one each, to the at least three continuous fluid channels for measuring, during operation of the catheter arrangement, a pressure drop at a respective continuous fluid channel through which the liquid flows, and wherein the pressure evaluation unit is formed with at least three channels for evaluating the signals from the at least three flow sensors for calculating a force vector of a force applied to the distal end of the catheter.

* * * * *